(12) United States Patent
Kawanami et al.

(10) Patent No.: US 6,310,476 B1
(45) Date of Patent: Oct. 30, 2001

(54) EDDY CURRENT FLAW DETECTOR

(75) Inventors: Seiichi Kawanami; Masaaki Kurokawa; Takeo Kamimura, all of Takasago (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 09/091,022

(22) PCT Filed: Mar. 21, 1997

(86) PCT No.: PCT/JP97/00936

§ 371 Date: May 24, 2000

§ 102(e) Date: May 24, 2000

(87) PCT Pub. No.: WO98/15822

PCT Pub. Date: Apr. 16, 1998

(30) Foreign Application Priority Data

Oct. 9, 1996 (JP) .................................................. 8-268742

(51) Int. Cl.⁷ ............................. G01N 27/82; G01R 33/12
(52) U.S. Cl. ......................... 324/241; 324/242; 324/243; 324/225
(58) Field of Search ..................................... 324/234, 235, 324/237, 238, 239, 240, 241, 242, 243, 225, 207.26

(56) References Cited

U.S. PATENT DOCUMENTS 4,677,379 * 6/1987 Arnaud et al. ........................ 324/242
5,510,709 * 4/1996 Hurley et al. ........................ 324/242

FOREIGN PATENT DOCUMENTS 51-151590  12/1976  (JP) .
5-133940   5/1993   (JP) .

OTHER PUBLICATIONS

Microfilm of the specification and drawings annexed to the written application of Japanese Utility Model Application No. 37485/1972.

* cited by examiner

Primary Examiner—Benjamin R. Fuller
Assistant Examiner—Henry S. Andersen
(74) Attorney, Agent, or Firm—Wenderoth, Lind & Ponack, L.L.P.

(57) ABSTRACT

This invention prevents the failure of detection for horizontal and oblique lift-offs in a probe for an eddy current flaw detection test. A plurality of probes are provided, and each probe includes four detection coils. Two adjacent eddy current flaw detecting probes commonly own (share) one of the four coils. The detection coils are connected to a bridge circuit for picking up a flaw signal. The detection coils are adjusted so that interlinkage magnetic fluxes generated inside the detection coils by the eddy current become equal. An excitation coil for inducing the eddy current in a test piece by AC driving can be disposed over the detection coils. The center of the excitation coil is positioned on the center axes of the detection coils. An oscillator for applying an AC current to this excitation coil is connected to the coil.

2 Claims, 10 Drawing Sheets

EDDY CURRENT FLAW DETECTOR

BACKGROUND OF THE INVENTION

1. Field of the Invention

The present invention relates to an eddy current flaw detecting probe used for an eddy current test to determine an internal flaw non-destructively.

2. Description of the Prior Art

An eddy current test is now widely practiced for tests in manufacturing iron and steel material and non-ferrous metal material, and maintenance inspection tests in various plants including small diameter tubes for heat exchangers and the like. An eddy current flaw detecting probe is one of the important factors which decide performance of a flaw detector.

One example of a prior art eddy current flaw detecting probe is shown in FIG. 11. Numeral 1 designates a test object, numeral 50 designates an exciting and detecting coil, numeral 51 designates an exciting coil and numeral 52 designates a detecting coil. In the prior art eddy current flaw detecting probe, there are used a bobbin coil, a pancake coil and the like as the exciting detecting coil. The flaw detecting probe is divided into an absolute type [FIGS. 11(a) and (b)] for testing for the presence of a flaw by impedance change in the respective coils 50, 52 and a differential type [FIGS. 11(c), (d) and (e)] for the presence of a flaw by differential component in the two coils 50, 52.

Also, the flaw detecting probe is divided into a self-induction type [FIGS. 11(a), (c) and (e)], in which the same coil 50 carries out both excitation for inducing eddy current and detection of magnetic field by the eddy current, and a mutual induction type [FIGS. 11(b) and (d)] which comprises two kinds of coil including the exciting coil 51 for excitation and the detecting coil 52 for detection.

The differential type, especially, has an advantage (as compared with the absolute type) in dealing with noises caused by horizontal lift-offs in which a distance between the coil and the test object changes. In the prior art eddy current flaw detecting probe (especially of the absolute type), lift-off signals due to lift-offs occur so that a flaw signal may be buried, which results in problems such as a reduction in detecting power.

Further, even in the differential type which is during generally good for lift-offs, during an inclined lift-off (FIG. 12) in which the probe inclines relative to the test object, there occurs a difference in distance $1_1$ and $1_2$ from the two coils to the test object 1. This difference causes inclined lift-off signals, which result in problems such as a reduction in the flaw detecting power. It is to be noted that numeral 51 designates an exciting coil.

Also, in the eddy current flaw detecting probe shown in FIG. 11(e), there is less reduction in the detecting power against the inclined lift-off. This probe is constructed such that two coils, arranged so as to cross each other, are mutually in a differential connection. This probe has, however, a directivity in the detecting power and there is a shortcoming that it has especially less flaw detecting power in the angle of 45° to a scanning direction.

SUMMARY OF THE INVENTION

It is therefore an object of the present invention to provide an eddy current flaw detecting probe in which detecting power does not lower during lift-offs, and which has improved directivity.

In order to attain this objection, the present invention provides an eddy current flaw detecting probe constructed as follows.

(1) An eddy current flaw detector of the present invention includes an eddy current flaw detecting probe having coils for detecting displacement in a magnetic field due to eddy current induced in a test object by alternating current drive. The eddy current flaw detecting probe comprises two coils, having mutually different diameters, which are arranged coaxially and are in a differential connection with each other.

In this case, the construction is preferably a mutual induction type in which the two coils are detecting coils and in which an exciting coil is provided coaxially with the two detecting coils.

(2) Another eddy current flaw detector of the present invention includes an eddy current flaw detecting probe having coils for detecting displacement in a magnetic field due to eddy current induced in a test object by alternating current drive. The eddy current flaw detecting probe is constructed such that each one of the coils is arranged so as to have its center at each apex portion of a lozenge. A pair of the coils arranged on a diagonal of the lozenge are in a common mode connection with each other, and two sets of the pair of coils in the common mode connection are in a differential connection with each other.

(3) Another eddy current flaw detector of the present invention is a self-induction type including an eddy current flaw detecting probe having coils for measuring displacement in a magnetic field due to eddy current induced in a test object by alternating current drive. The eddy current flaw detecting probe is constructed such that each one of the coils having the same characteristics is arranged so as have its center at each apex portion of a lozenge. A pair of the coils arranged at the apex portion on a diagonal of the lozenge are in a reverse mode connection with each other, and two sets of the pair of coils in the reverse mode connection are in a differential connection with each other.

(4) Another eddy current flaw detector of the present invention is similar to those described above. However, the eddy current flaw detecting probe is formed and arranged in a plural number, and two adjacent eddy current flaw detecting probes thereof commonly own one coil out of four coils. Each one of the coils has its center at each apex portion of the lozenge, and there is a means for switching the eddy current flaw detecting probes.

In this case, there are arranged a plurality of eddy current flaw detecting probes on a side face of a column-like base substance.

In each of the above-mentioned constructions, the coils for detecting a magnetic field are adjusted so that interlinkage magnetic fluxes become equal unless there is a flaw in the test object.

According to the eddy current flaw detecting probes of the present invention constructed as described above, the following functions and effects can be obtained.

In the eddy current flaw detector of (1) above, it is preferable to adjust a signal ratio electrically so that signals from the two detecting coils are cancelled when there is no flaw, or to adjust a winding number ratio of the two coils so that interlinkage magnetic fluxes of the two coils become equal when there is no flaw.

If the above probes are constructed in the self-induction type, because there are differences in diameters and winding numbers of the two coils, there occurs a phase difference in the exciting signals generated at the respective coils to cause an irregularity in the distribution of the alternating magnetic field. But if they are constructed in the mutual induction type, the excitation does not relate to the state of the coil and there occurs no irregularity in the distribution of the magnetic field.

Also, if the flaw detecting probe scans a portion where there is a flaw, the eddy current in the vicinity of the flaw in the test object changes and irregularity occurs in the alternating magnetic field generated by the eddy current. The irregularity in the magnetic field is detected first in the coil having a larger diameter. Thus, there occurs a difference in the interlinkage magnetic fluxes of the two coils and the flaw is detected.

In case there is a change in the horizontal lift-off, the distance between the flaw detecting probe and the test object changes. However, because the two coils are arranged on a concentric circle, the interlinkage magnetic fluxes become equal so that a difference therein becomes zero and no lift-off signal is detected. Also, if there is a change in the inclined lift-off as shown in FIG. 13, the distance 1 from the centers of the two coils 2 (2a, 2b) to the test object 1 are equal as to the respective coils so that the difference in the interlinkage magnetic fluxes between the coils 2 is small and reduction of the lift-off signals can be attained. Further, because there is induced a circular eddy current on the test object 1 by the exciting coil 4, detection of flaw in every direction becomes possible.

According to the eddy current flaw detector of (2) above, eddy current is induced in the test object by excitation, and a change in this eddy current is detected by the detecting coil which couples magnetically. The four detecting coils are constructed such that two coils on the diagonal are in the common mode connection with each other and two sets of these two coils in the common mode connection are in the differential connection with each other, which is seen as if two coils are in the differential connection.

The detection centers of the two sets of detecting coils in the differential connection are the same because the four coils are arranged such that each coil is arranged on each apex portion of a lozenge. Thus, changes in the horizontal lift-off are completely cancelled between the two coils in the common mode connection. Also, for the inclined lift-off as shown in FIG. 14, the detection centers of the two sets of coils 20, in the common mode connection are the same. Thus, even if the test object inclines, because the distance 1 between the detection centers and the test object does not change between each other, the lift-off signals can be greatly reduced.

It is to be noted that a common mode connection means a connection with a polarity of coil being in the same direction, and a differential connection means a connection so as to create a difference in an output voltage. The common mode connection and the differential connection are shown in FIG. 15 in an equivalent circuit-wise expression. These connections can be expressed also as shown in FIG. 15(b). In FIG. 15, a black spot shows a polarity of each coil and an arrow shows a direction of voltage generated by each coil. In FIG. 15, numerals 60a to 60d designate detecting coils and numerals 61a to 61d designate exciting coils. The coils 60a and 60b are arranged at apex portions on a diagonal of a lozenge and the coils 60c and 60d are arranged likewise at apex portions on the other diagonal of the lozenge. The coils 60a and 60b are connected with a polarity of each coil being in the same direction, that is, in the common mode connection. Likewise, coils 60c and 60d are in the common mode connection. A set of the coils 60a and 60b and a set of coils 60c and 60d are connected so as to take a difference in the output voltage, that is, in the differential connection.

According to the eddy current flaw detector of (3) above, coils of the same characteristics are arranged at apex portions of a lozenge. The coils arranged on a diagonal are in the reverse mode connection, and two sets of the two coils in the reverse mode connection are in the differential connection. This example is shown concretely in FIG. 16. It is to be noted that the actual construction of this example is of the self-induction type but for purpose of easy understanding it is shown here in the mutual induction type in which polarities of excitation and detection are the same. In FIG. 16, numerals 70a to 70d designate detecting coils, and numerals 71a to 71d designate exciting coils. The coils 70a and 70b are arranged at apex portions on a diagonal of a lozenge, and the coils 70c and 70d are arranged likewise at apex portions on the other diagonal of the lozenge. The coils 70a and 70b are connected with a polarity of reverse direction, but because the polarity of the exciting coils 71a and 71b are reversed, output voltage of the two coils 70a and 70b becomes the sum thereof (This is called a reverse mode connection). Also, the coils 70c and 70d are in the reverse mode connection. The set of the coils 70a and 70b and the set of the coils 70c and 70d are in the differential connection so as to create a difference in the output voltages.

According to the eddy current flaw detector of (4) above, in addition to the construction of arrangement of the probes described in (2) or (3) above, sensors are formed and arranged in a plural number and the sensors are overlapped portionally with each other. Hence, dead angle in the detection sensitivity in the direction of arrangement can be reduced.

DESCRIPTION OF THE PREFERRED EMBODIMENTS

Herebelow, description will be made on embodiments according to the present invention with reference to the figures.

(First Embodiment)

Figure 1A:
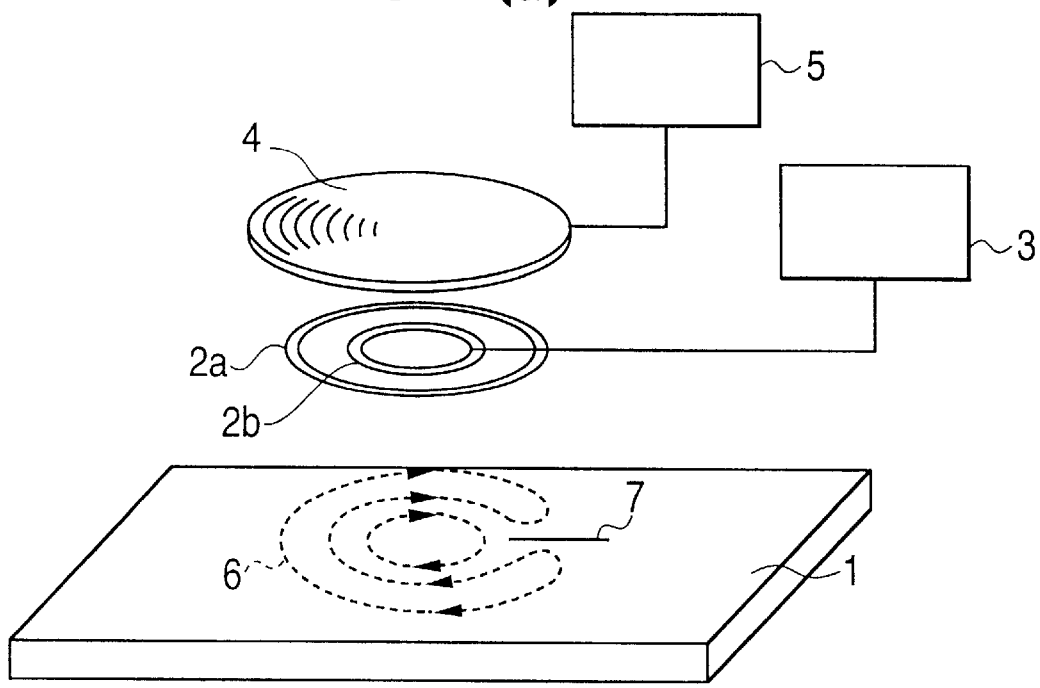
FIG. 1 is a view showing construction of an eddy current flaw detecting probe of a first embodiment according to the present invention.
Figure 1B:
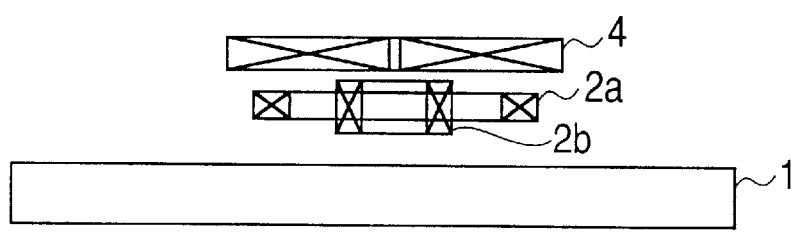

FIG. 1 is a view showing construction of an eddy current flaw detecting probe of a first embodiment according to the present invention, wherein FIG. 1(a) is a schematic perspective view of the eddy current flaw detecting probe and FIG. 1(b) is a cross sectional view thereof. Over a surface of test object 1 are arranged two detecting coils 2 (2a, 2b) which are concentric with, and have different diameters with respect to each other. The two detecting coils 2a, 2b, which are in a differential connection with each other, are connected to a bridge circuit 3 for picking up a flaw signal only. The two detecting coils 2a, 2b are so adjusted in advance that there occur equal interlinkage magnetic fluxes in the detecting coils 2 by the eddy current unless there is a flaw in the test object 1.

Also, over the two detecting coils 2, there is arranged an exciting coil 4 for inducing eddy current in the test object by alternating current drive. The center of the exciting coil 4 is on the central axis of the detecting coil 2. The exciting coil 4 is connected to an oscillator 5 for supplying the exciting coil 4 with an alternating current.

In the present detector, output of the bridge circuit 3 becomes zero unless there is a flaw. If there is a flaw, there occurs an output in the bridge circuit 3 and the flaw can be detected.

The function of the present detector will be described. Firstly, an alternating current is supplied to the exciting coil 4 from the oscillator 5 to generate an alternating magnetic field and induce an eddy current 6 in the surface of the test object 1. The detecting coil 2 detects a change in a magnetic field generated by the eddy current 6.

Unless there is a flaw in the area where the eddy current 6 is induced, the eddy current 6 is in a regular state. In the eddy current 6 of the regular state, signals are cancelled by the detecting coils 2a, 2b, which are so adjusted that the interlinkage magnetic fluxes become equal in that state, and output of the bridge circuit 3 becomes zero. On the other hand, if there is a flaw 7 in the test object 1, there occurs an irregularity in the eddy current 6 to cause a difference in the interlinkage magnetic fluxes in the detecting coils 2a, 2b of the inside and the outside. Thus, the difference in the interlinkage magnetic fluxes is detected by the bridge circuit 3 and the flaw 7 is detected.

Further, if there is a horizontal lift-off, because the two detecting coils are concentric and the interlinkage magnetic fluxes become equal, lift-off signals are cancelled and output of the bridge circuit becomes zero. In case of an inclined lift-off, because detection centers of the two detecting coils are at an equal distance each other from the test object, there is only a small difference in the interlinkage magnetic fluxes in the two detecting coils and lift-off signals are reduced.

Figure 2:
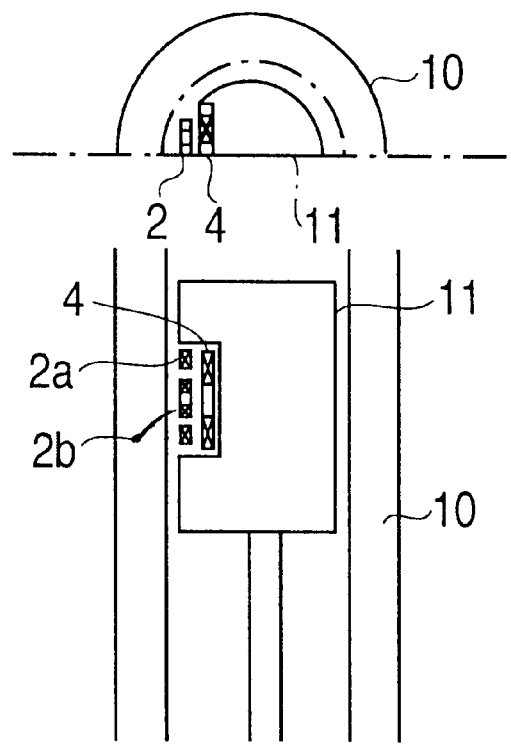
FIG. 2 is a view showing an example in which the eddy current flaw detecting probe of FIG. 1 is applied to a cylindrical test object.

Next, description will be made with reference to FIG. 2 in a case where the construction of the present embodiment is used for testing the interior of a cylindrical test object such as a small diameter tube etc. Here, the same parts as those in FIG. 1 are given the same numeral and description thereof is omitted. In the test of a cylindrical test object such as a small diameter tube etc., the exciting coil 4 and the detecting coil 2 are fitted to a probe base substance 11, for example. If the cylindrical test object 10 has a curvature, the probe becomes inclined relative to the central axis of the cylindrical test object 10. Nevertheless, by use of this probe, horizontal lift-off signals can be cancelled and inclined lift-off signals can be reduced. Thus, a flaw detecting power can be enhanced.

Figure 3:
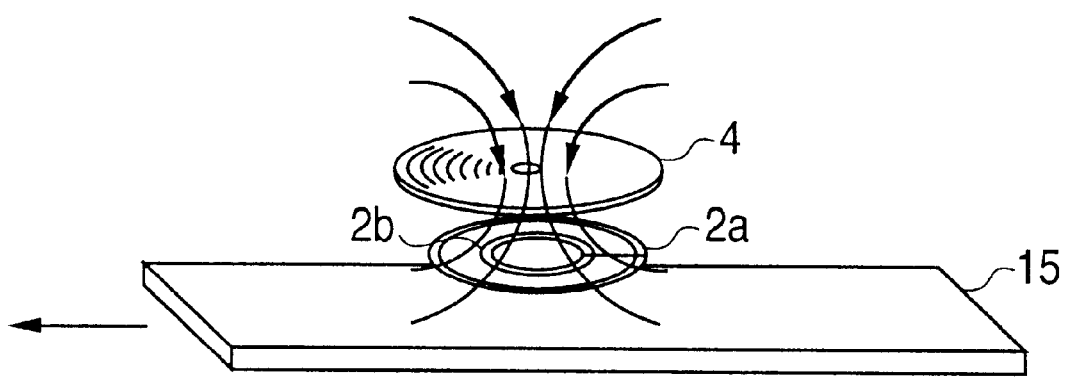
FIG. 3 is a view showing an example in which the eddy current flaw detecting probe of FIG. 1 is applied to a rolling process.

Next, a case where the present embodiment is used for testing an iron plate in a rolling process will be described with reference to FIG. 3. In case an eddy current test is to be done on an iron plate 15 in a rolling process, there is no constant lift-off of the iron plate 15 which moves at a high velocity on a moving device such as a roller etc. By use of the probe of the present invention, however, lift-off signals can be reduced, flaw detecting power can be enhanced and quality of the iron plate can be maintained.

(Second Embodiment)

Figure 4A:
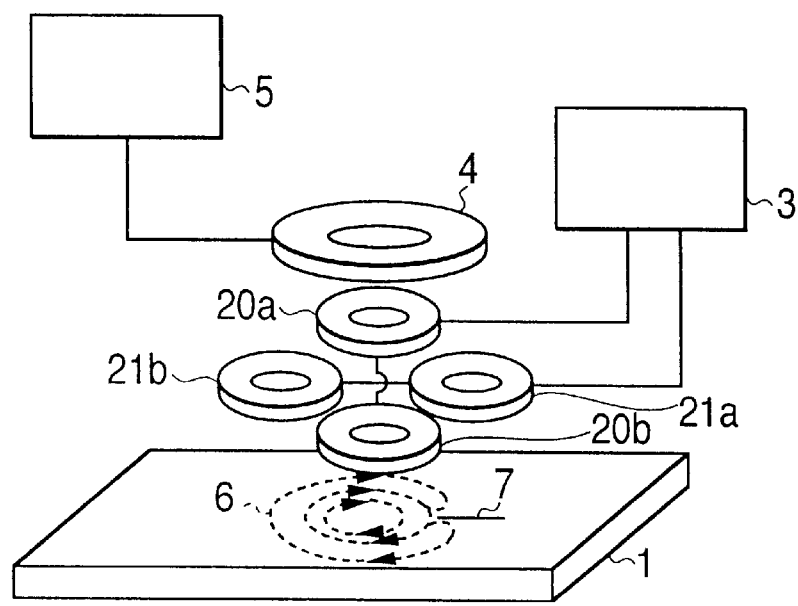
FIG. 4 is a view showing construction of an eddy current flaw detecting probe of a second embodiment according to the present invention.
Figure 4B:
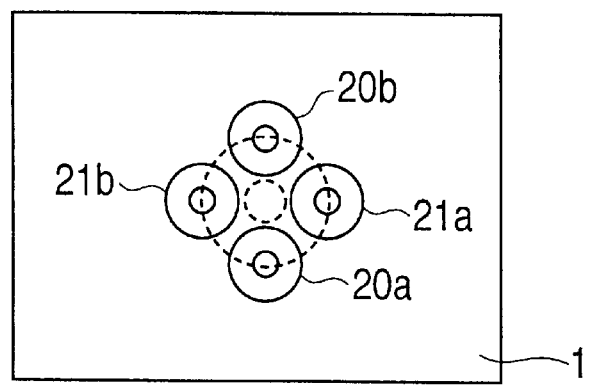
Figure 4C:
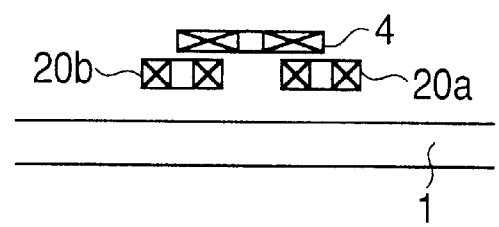
Figure 5:
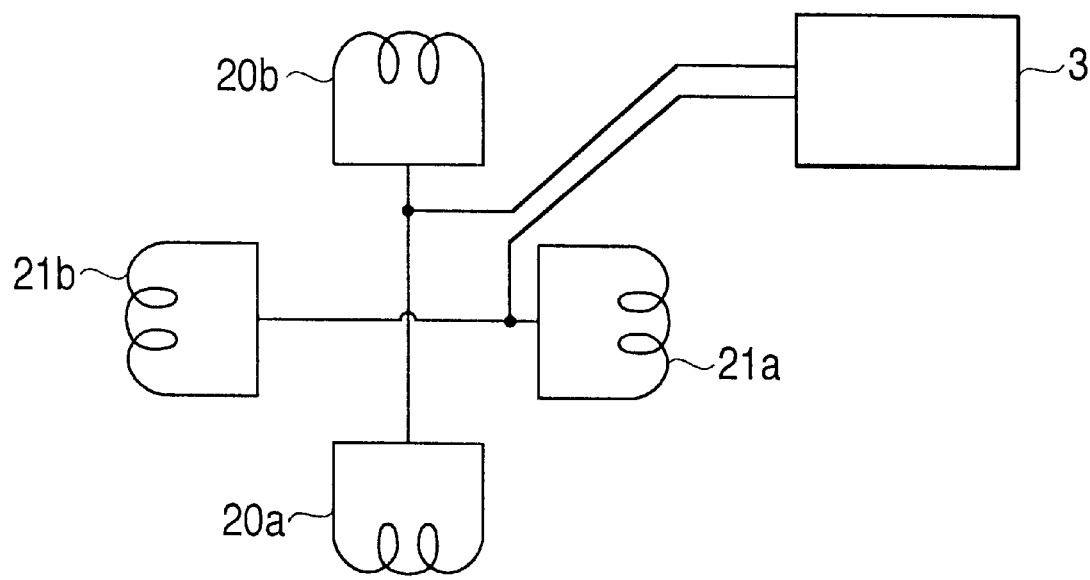
FIG. 5 is a view showing a circuit of detecting coils in the eddy current flaw detecting probe of FIG. 4.

FIG. 4 is a schematic view showing the concept of an eddy current flaw detecting probe of a second embodiment according to the present invention, wherein FIG. 4(a) is a perspective view of the eddy current flaw detecting probe, FIG. 4(b) is a plan view thereof and FIG. 4(c) is a cross sectional view of the same. Also, FIG. 5 is a schematic view showing circuit construction of a detecting coil portion of the eddy current flaw detecting probe of the present embodiment. Over a test object 1 are arranged four detecting coils 20 (20a, 20b), 21 (21a, 21b) such that each coil thereof has its center, at each apex portion of a lozenge. The four detecting coils 20a, 20b, 21a, 21b are so adjusted that there occur equal interlinkage magnetic fluxes when an eddy current 6 is in a regular state.

The two detecting coils 20a and 20b, and 21a and 21b, respectively, arranged on a diagonal, are in a common mode connection with each other, and two sets of the detecting coils 20 and 21 in the common mode connection are in a differential connection with each other and are connected to a bridge circuit 3 for picking up a flaw signal. Also, over the detecting coils 20, 21, there is arranged an exciting coil 4 for inducing an eddy current 6 in a test object 1. The exciting coil 4 is connected to an oscillator 5 for supplying the exciting coil 4 with an alternating current.

In the present detector, unless there is a flaw, output of the bridge circuit 3 becomes zero. If there is a flaw, output of the bridge circuit 3 appears and the flaw can be detected.

The function of the present apparatus will be described. An alternating current is supplied to the exciting coil 4 from the oscillator 5 to induce an eddy current 6 in the surface of the test object 1. By this eddy current 6, an alternating magnetic field is generated and interlinkage magnetic fluxes caused by the eddy current 6 pass through the detecting coils 20, 21 so that an electric current occurs in the detecting coils 20, 21.

Unless there is a flaw, the eddy current is in a constant state to make the interlinkage magnetic fluxes in the detecting coils 20, 21 equal so that output of the bridge circuit 3 becomes zero. If there is a flaw, the eddy current becomes irregular so that the interlinkage magnetic fluxes in the detecting coils 20, 21 become different between each of the coils so that output of the bridge circuit 3 appears and the flaw can be detected.

Further, if there is a horizontal lift-off, because there is no difference between the two sets of the detecting coils 20, 21 in the distance from detection centers of the two sets of the detecting coils 20, 21 in the common mode connection to the test object 1, lift-off signals are cancelled for a change of parallel lift-off. Likewise for an inclined lift-off, lift-off signals are reduced greatly.

Figure 6:
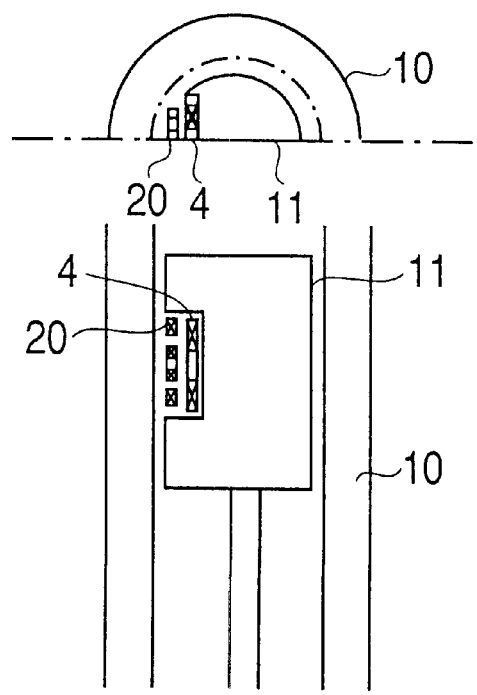
FIG. 6 is a view showing an example in which the eddy current flaw detecting probe of FIG. 4 is applied to a cylindrical test object.

Next, description will be made with reference to FIG. 6 for a case where the construction of the present embodiment is used for testing the interior of a cylindrical test object such as a small diameter tube etc. Here, the same parts as those in FIG. 4 are given the same numerals and description thereof is omitted. In case the cylindrical test object 10 has a curvature, a probe 11 becomes inclined relative to the central axis of the cylindrical test object 10. But by use of this probe 11, horizontal lift-off signals can be cancelled and inclined lift-off signals can be reduced. Thus, a flaw detecting power can be enhanced.

Figure 7:
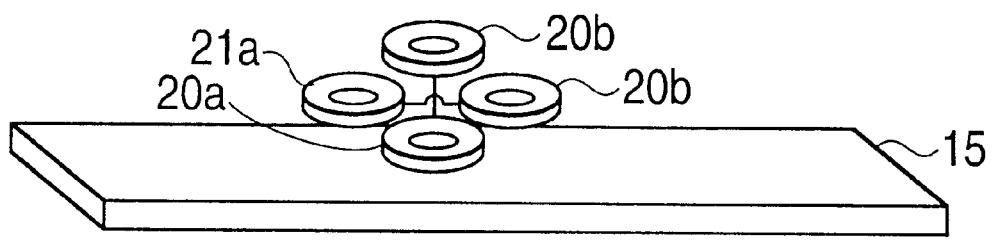
FIG. 7 is a view showing an example in which the eddy current flaw detecting probe of FIG. 4 is applied to a rolling process.

Next, a case where the present embodiment is used for testing an iron plate in a rolling process will be described with reference to FIG. 7. Here, the same parts as those shown in FIG. 4 are given the same numerals and description thereof is omitted. In case an eddy current test is to be done on an iron plate 15 in a rolling process, there is no constant lift-off of the iron plate 15 which moves at a high velocity on a moving device such as a roller etc. By use of the probe of the present embodiment, however, lift-off signals can be reduced, flaw detecting power can be enhanced and quality of the iron plate can be maintained.

(Third Embodiment)

Figure 8:
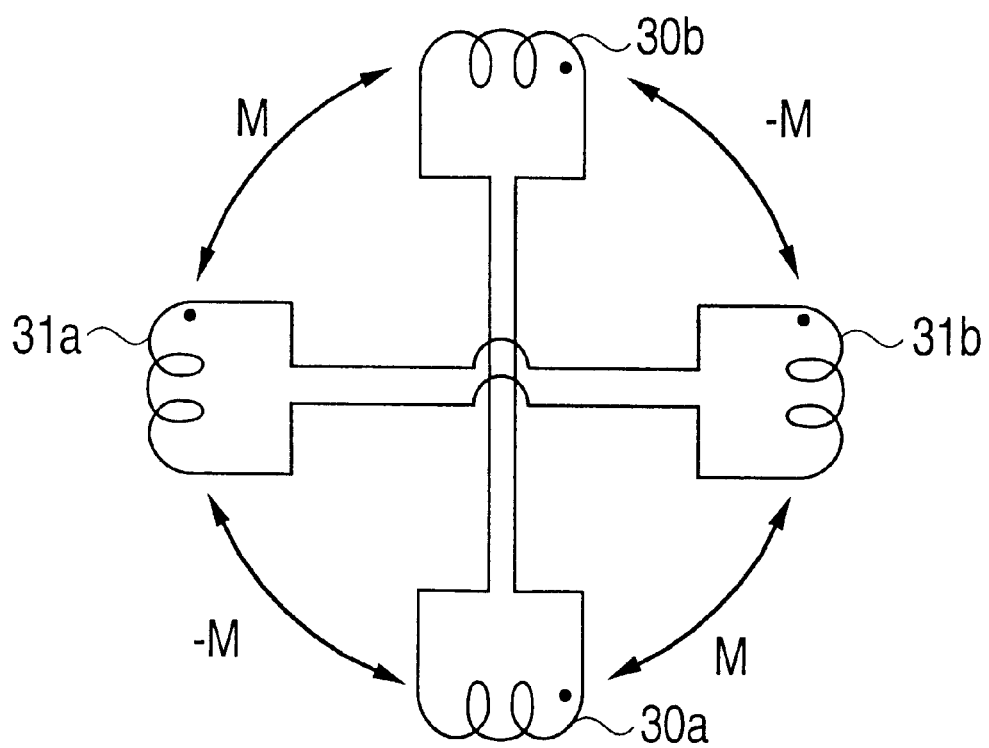
FIG. 8 is a view showing a circuit of an eddy current flaw detecting probe of a third embodiment according to the present invention.

FIG. 8 is a schematic view showing the circuit construction of an eddy current flaw detecting probe of a third embodiment according to the present invention. It is to be noted that the eddy current flaw detecting probe of the present embodiment is driven in a self-induction type in which the same coil carries out both excitation and detection. Also, a black spot in the figure shows a polarity of the coil.

Two coils 30a and 30b, and 31a and 31b, respectively, arranged on a diagonal, are connected in a reverse polarity with respect to each other. The two sets of coils 30 (30a, 30b) and 31 (31a, 31b), respectively, in a reverse mode connection, are in a differential connection with each other. Each of the detecting coils 30a, 30b is positioned at one apex portion on a diagonal of a lozenge and each of the detecting coils 31a, 31b is positioned at one apex portion on the other diagonal of the lozenge.

With the above circuit construction, the coil 30a, for example, has a direction of the current reversed relative to the adjacent coils 31a, 31b. As the result, mutual induction which the coil 30a receives from the coils 31a, 31b is set off. That is, even if a variation occurs in the current in the coils 31a, 31b, the coil 30a is not affected thereby. Likewise as to the coils 30b, 31a, 31b, the respective coils are not affected by a variation in the adjacent coils.

(Fourth Embodiment)

Figure 9:
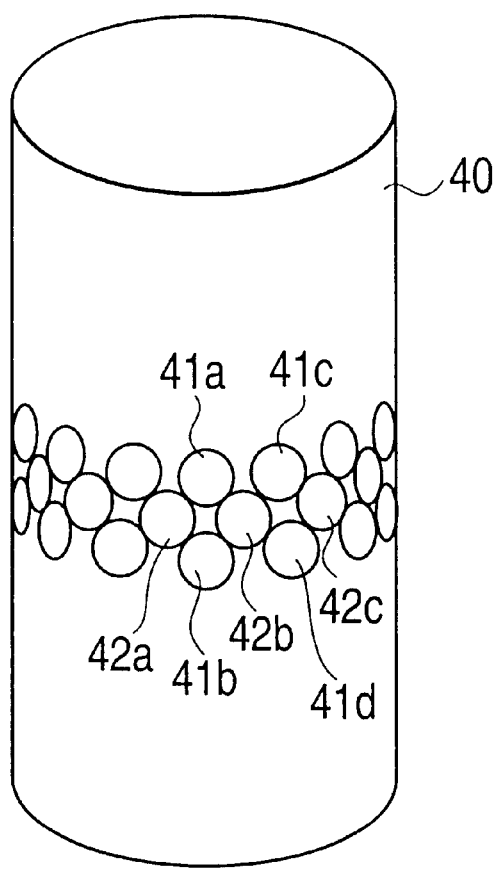
FIG. 9 is a view showing an eddy current flaw detecting probe of a fourth embodiment according to the present invention.

FIG. 9 is a schematic view showing construction of an eddy current flaw detecting probe of a fourth embodiment according to the present invention. A tube testing probe of the present embodiment is constructed such that the coils of the second embodiment, for example, are arranged on a circumference of a column-like probe base substance 40. One eddy current flaw detecting probe consists of four coils 41a, 41b, 42a, 42b. Also, one eddy current flaw detecting probe consists of four coils 41c, 41d, 42b, 42c. That is, the coil 42b is commonly owned (shared) by the two adjacent eddy current flaw detecting probes. Thus, probes (sensors) are formed on the entire circumference of the probe base substance 40. By each of these sensors being switched electrically, the tube interior is tested along the circumferential direction and by the same being moved along the axial direction, the tube is tested along its entire length.

Figure 10:
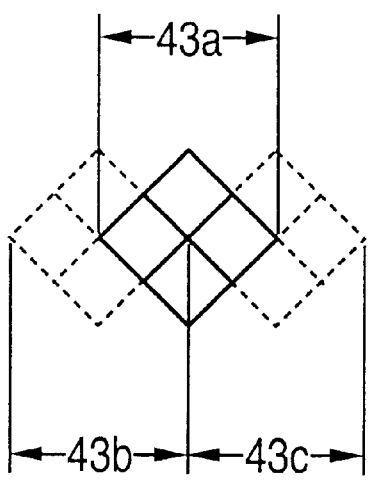
FIG. 10 is an explanatory view of the probe of FIG. 9.
Figure 11A:
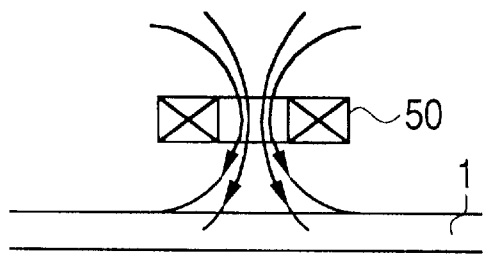
FIG. 11 is a view showing a prior art eddy current flaw detector.
Figure 11C:
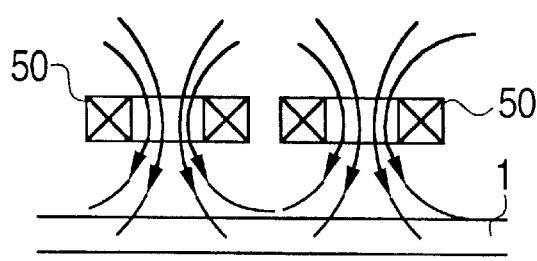
Figure 11B:
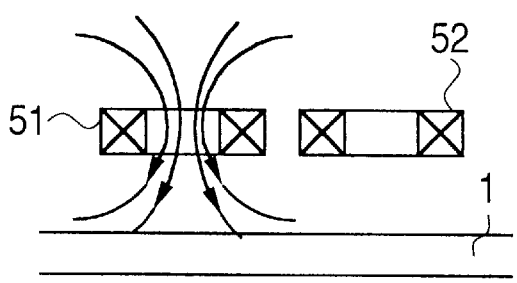
Figure 11D:
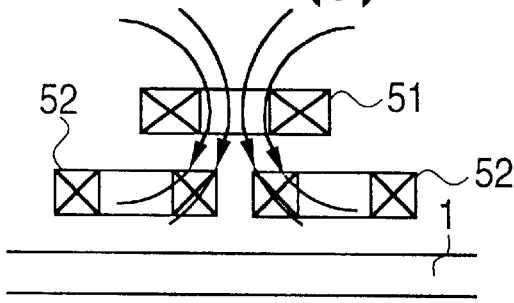
Figure 11E:
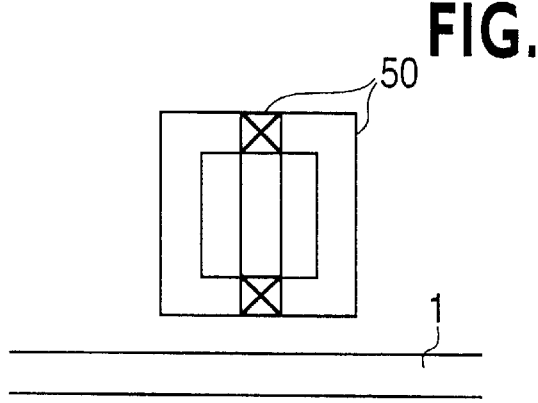
Figure 11E:
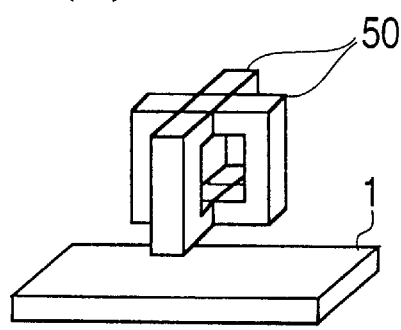
Figure 12:
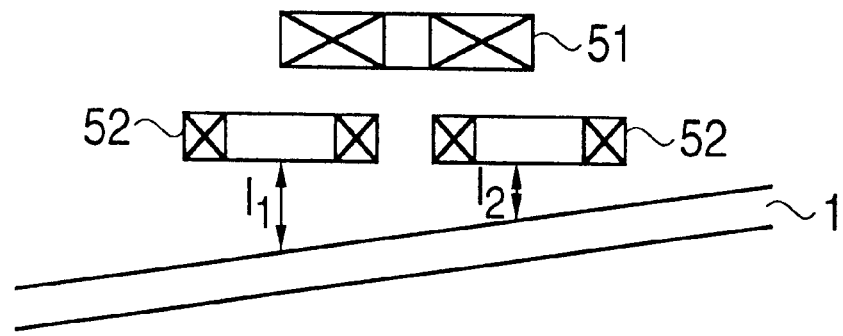
FIG. 12 is an explanatory view of inclined lift-off of the prior art eddy current flaw detecting probe.
Figure 13:
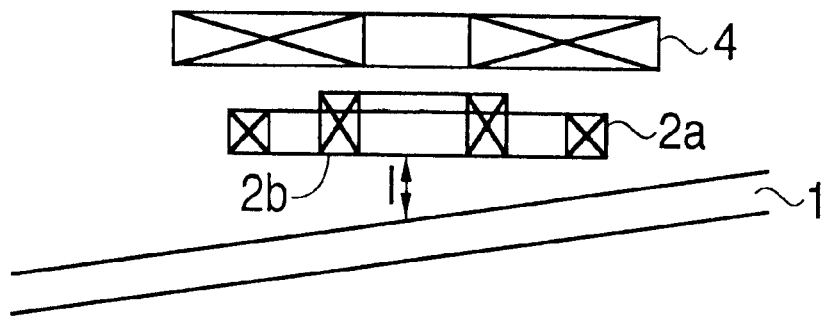
FIG. 13 is a view showing an effect of the inclined lift-off of eddy current in the present invention.
Figure 14:
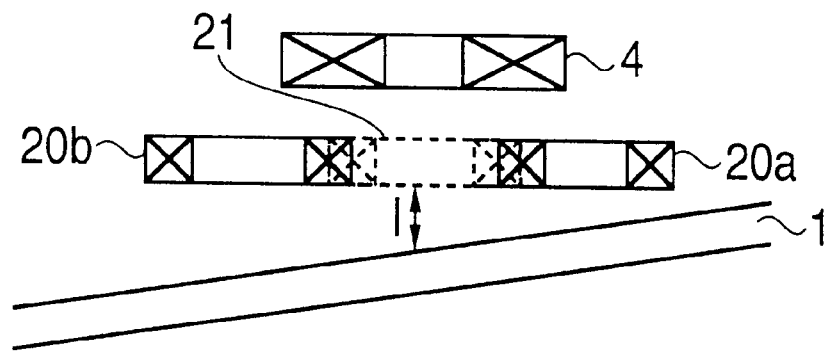
FIG. 14 is a view showing an effect of the inclined lift-off of eddy current in the present invention.
Figure 15A:
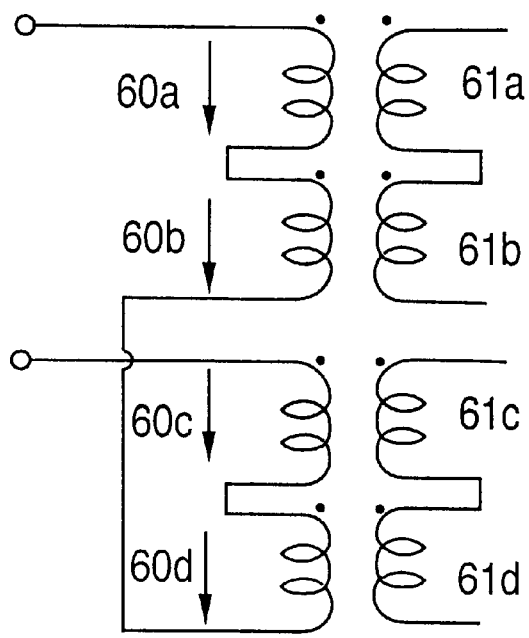
FIG. 15 is a view of an equivalent circuit for explaining the concept of the present invention.
Figure 15B:
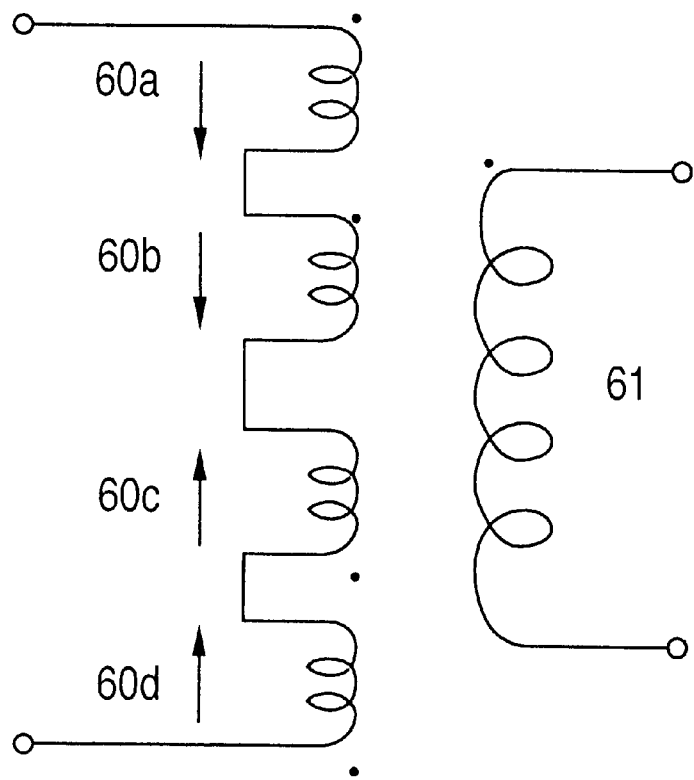
Figure 16:
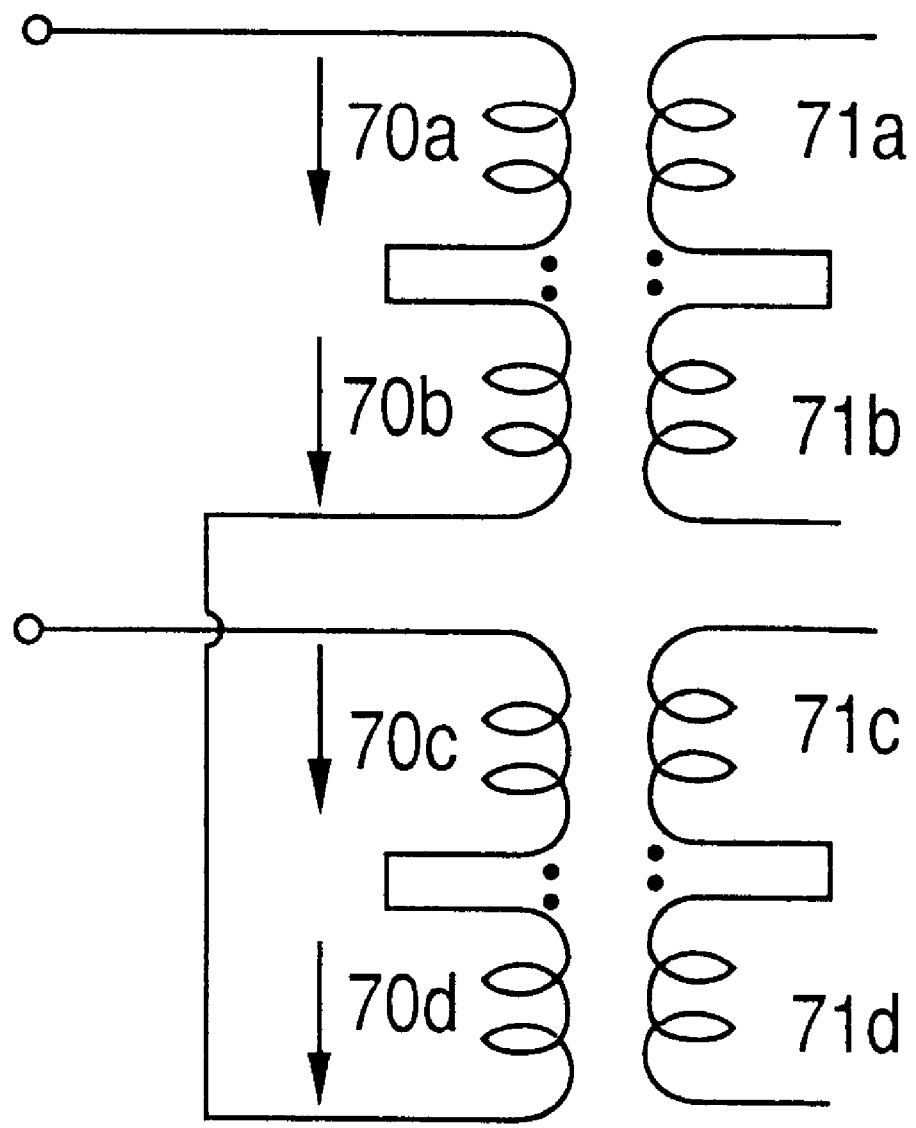
FIG. 16 is a view of an equivalent circuit for explaining the concept of the present invention.

According to the present embodiment, a coil is commonly owned by the adjacent sensors. Hence, the number of coils in the circumferential direction can be lessened. Also, if four coils as shown in FIG. 10 are regarded as one sensor, a sensor 43b is overlapped portionally by sensors 43b, 43c in the circumferential direction. Hence, there can be reduced a dead angle in the detection sensitivity in the circumferential direction.

It is to be noted that the invention is not limited to the embodiments described above. For example, in the fourth embodiment wherein the plurality of sensors are formed and arranged on the side face of the column, the sensors may be formed and arranged on a base substance of other type than the column.

Also, the invention may be practiced with various modifications.

Industrial Applicability

The eddy current flaw detecting apparatus according to the present invention is constructed such that two sets of detecting coils are arranged to have the same detection center and these two sets of detecting coils are in a differential connection. Thus, horizontal lift-off signals can be cancelled completely and inclined lift-off signals can be reduced.

What is claimed is:

1. An eddy current flaw detector comprising:

a plurality of eddy current flaw detecting probes, each of said eddy current flaw detecting probes including four coils for detecting displacement of a magnetic field due to eddy current induced in an object to be tested by alternating current, said coils of each of said eddy current flaw detecting probes being arranged such that a center of each of said coils is located at an apex of a lozenge and so as to form a first pair of coils and a second pair of coils, said first pair of coils being arranged on a diagonal of said lozenge and being connected in a common mode, said second pair of coils being arranged on a diagonal of said lozenge and being connected in a common mode, said first pair of coils being connected to said second pair of coils in a differential mode, wherein adjacent eddy current flaw detecting probes share a common one of said four coils; and a mechanism for switching operation of each of said eddy current flaw detecting probes.

2. A self-induction eddy current flaw detector comprising:

a plurality of eddy current flaw detecting probes, each of said eddy current flaw detecting probes including four coils for measuring displacement of a magnetic field due to eddy current induced in an object to be tested by alternating current, said coils of each of said eddy current flaw detecting probes being arranged such that a center of each of said coils is located at an apex of a lozenge and so as to form a first pair of coils and a second pair of coils, said first pair of coils being arranged on a diagonal of said lozenge and being connected in a reverse mode, said second pair of coils being arranged on a diagonal of said lozenge and being connected in a reverse mode, said first pair of coils being connected to said second pair of coils in a differential mode, wherein adjacent eddy current flaw detecting probes share a common one of said four coils; and a mechanism for switching operation of each of said eddy current flaw detecting probes.

* * * * *